US00PP19991P3

(12) United States Plant Patent

Werner et al.

(10) Patent No.: US PP19,991 P3

(45) Date of Patent: May 12, 2009

(54) *BUDDLEJA* PLANT NAMED 'BLUE CHIP'

(50) Latin Name: *Buddleja davidii*
Varietal Denomination: Blue Chip

(75) Inventors: Dennis James Werner, Raleigh, NC (US); Layne Karlton Snelling, Cary, NC (US)

(73) Assignee: North Carolina State University, Raleigh, NC (US)

( * ) Notice: Subject to any disclaimer, the term of this patent is extended or adjusted under 35 U.S.C. 154(b) by 78 days.

(21) Appl. No.: 11/894,885

(22) Filed: Aug. 23, 2007

(65) Prior Publication Data

US 2009/0055981 P1 Feb. 26, 2009

(51) Int. Cl.
*A01H 5/00* (2006.01)

(52) U.S. Cl. ..... Plt./242

(58) Field of Classification Search ..... Plt./242
See application file for complete search history.

(56) References Cited

PUBLICATIONS

UPOV ROM GTITM Computer Database, GTI Jouve Retrieval Software 2008/01 Citation for 'Blue Chip'.*

* cited by examiner

*Primary Examiner*—Wendy C. Haas

(57) ABSTRACT

*Buddleja* 'Blue Chip' is a new and distinct variety of butterfly bush that has the following unique combination of desirable features that are outstanding in a new variety.

1. Moderate vigor resulting in compact growth habit.
2. Ease of asexual propagation using softwood or semi-hardwood cuttings.
3. Spreading growth habit with multi-branched stems.
4. Male sterility, and low female fertility and reduced seed set, resulting in less opportunity for seedlings to originate in the landscape setting.
5. Blue flower color.

3 Drawing Sheets

Latin name of the genus and species: Genus: *Buddleja.* Species: complex hybrid including *davidii, lindleyana,* and *globosa.*

Variety denomination: The inventive cultivar of *Buddleja* disclosed herein has been given the variety denomination 'Blue Chip'.

BACKGROUND OF THE INVENTION

The present invention relates to a new and distinct variety of *Buddleja davidii* (butterfly bush) grown as an ornamental shrub for home and commercial landscapes. Butterfly bush is typically grown for its attractive, fragrant flowers that are borne throughout the growing season.

The new and distinct variety of butterfly bush resulted from a formal breeding program established by the inventors in Raleigh, N.C. United States. One of the objectives of the breeding program was to develop a compact, spreading *Buddleja* with blue flower color. 'Blue Chip' originated as a third generation descendant from a hand pollinated cross of 'Honeycomb'×('Nanho Purple'×*Buddleja lindleyana*) made in 2001. 'Honeycomb' (unpatented) was released in 1997, and is described as a hybrid of *Buddleja davidii* and *Buddleja globosa.* 'Nanho Purple' (unpatented) is a semi-compact selection of *Buddleja davidii* var. nanhoensis. *Buddleja lindleyana* is a species native to China. All three parents are available in commerce.

The seeds resulting from the 2001 controlled hybridization process were harvested in fall of 2001 and germinated in a greenhouse in Raleigh, N.C. in the winter of 2002. The resulting 32 seedlings were planted in field trials in spring of 2002. These plants flowered in summer 2002, and seed was collected off of all plants and bulked. This bulk seed was germinated in a greenhouse in Raleigh, N.C. in the winter of 2003. The resulting 69 seedlings were planted in the field in spring of 2003. These plants flowered in summer 2003, and one plant, designated NC2003-7, was selected for its compact growth habit and attractive blue flowers. Open pollinated seed was collected off of NC2003-7. This bulk seed was germinated in a greenhouse in Raleigh, N.C. in the winter of 2004. The resulting 11 seedlings were planted in the field in spring of 2004. These plants flowered in summer 2004, and one plant, designated NC2004-9, was selected for its multi-branched, compact growth habit and attractive blue flowers. This original plant demonstrated characteristics identical to those subsequently expressed on other plants when propagated from stem cuttings. This single plant is the subject of the present invention 'Blue Chip'.

The distinguishing traits of 'Blue Chip' are compact growth habit, multi-branched stems, gray-green leaf color, and flowers that are blue in color. The cultural requirements for 'Blue Chip' are well-drained soil, full sun, and moderate moisture. 'Blue Chip' exhibits no serious pest or disease problems known to the inventors, except for occasional spider mite infestation during periods of hot, dry weather.

The closest comparison known to the inventors is the cultivar 'Ellen's Blue' (unpatented). Plants and flowers of this new variety differ from 'Ellen's Blue'. In direct comparisons of the 2 cultivars in the inventor's experimental trials, plants of 'Blue Chip' are consistently more compact, more highly branched, more dense, and produce less viable seed than 'Ellen's Blue'. 'Blue Chip' is distinctly different from all three of its original parents.

The first asexual propagation of 'Blue Chip' was conducted by the inventors in fall 2004 in Raleigh, N.C., and 'Blue Chip' has subsequently been propagated in the same location in years 2005 and 2006. In all cases, the original plant selection was propagated asexually by softwood to semi-hardwood stem cuttings. Such cuttings root readily under mist in about 14 to 21 days, and resume normal growth. Five plants derived from stem cuttings of the variety were established in test plots at Sandhills Research Station and the Horticultural Field Laboratory in 2005, and ten additional plants derived from stem cuttings of the variety were established at the Sandhills Research Station in 2007. During all asexual propagation, the characteristics of the original plant have been maintained. Plants derived from stem cuttings exhibit characteristics identical to those of the original plant, and no aberrant phenotypes have appeared.

Test plantings and performance evaluation over three years at the Sandhills Research Station and Horticulture Field Laboratory demonstrate this variety to be relatively consistent in its characteristics even under the different growing conditions associated with yearly climatic variation.

Plants of the new variety are only moderately vigorous after establishment in the field, being less vigorous and more compact than most cultivars of butterfly bush. Young plants have averaged about 0.4 meters of growth per year. Plants are spreading in growth habit. Flowering occurs in the first year of growth on newly formed wood. The inflorescence is a simple panicle, and shows a blue flower color. Flowering usually begins in late May to early June in Jackson Springs, N.C., and continues throughout the growing season until the first freeze event in October or November. An individual inflorescence flowers for about 7–10 days, depending on temperature, but new flowers are made during the entire growing season. Fertility of flowers is low, and the new cultivar sets very few seed, an asset-in landscape settings.

'Blue Chip' is distinguished from other related known cultivars based on the unique combination of traits including compact growth habit, multiple-branched stems, and blue flower color.

The new variety has been named the BLUE CHIP cultivar. No public sale of 'Blue Chip' has yet taken place at the time of application.

SUMMARY OF THE INVENTION

'Blue Chip' is a new and distinct variety of butterfly bush that has the following unique combination of desirable features outstanding in a new variety. In combination these traits set 'Blue Chip' apart from all other existing varieties of butterfly bush known to the inventors.

1. 'BLUE CHIP' has moderate vigor resulting in compact growth habit.
2. 'BLUE CHIP' is asexually propagated using softwood or semi-hardwood cuttings.
3. 'BLUE CHIP' demonstrates spreading growth habit and multi-branched stems.
4. 'BLUE CHIP' exhibits low female fertility and reduced seed set, resulting in less opportunity for seedlings to originate in the landscape setting.
5. 'BLUE CHIP' has blue flower color.

BRIEF DESCRIPTION OF THE DRAWINGS

The photographs in the drawings were made using digital photography techniques, and show the colors as true as reasonably possible by digital photography. Colors in the photographs may differ slightly from the color values cited in the detailed botanical description, which accurately describe the colors of the new *Buddleja* variety 'BLUE CHIP'. All photographs were taken from two-year-old plants growing at the Horticulture Field Laboratory, Raleigh, N.C.

Figure 1:
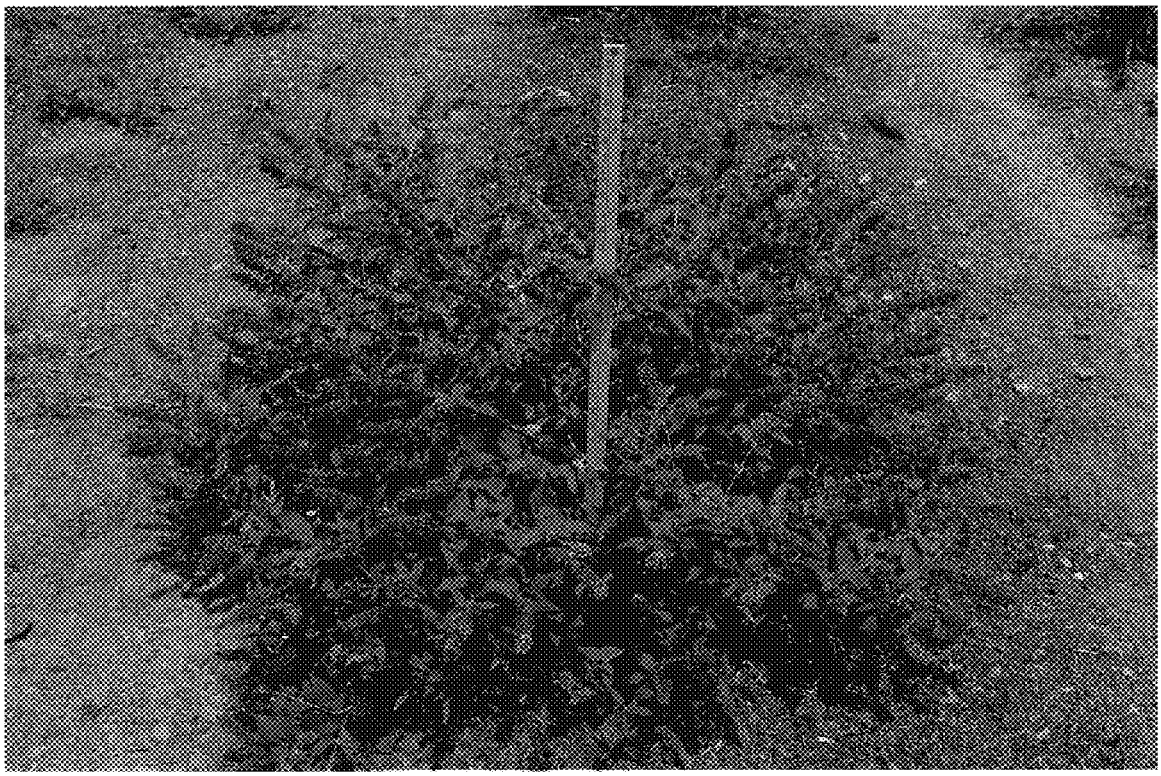
FIG. 1 shows a typical plant of 'BLUE CHIP', showing the compact growth, spreading habit, multi-branched stems, and blue flowers.
Figure 2:
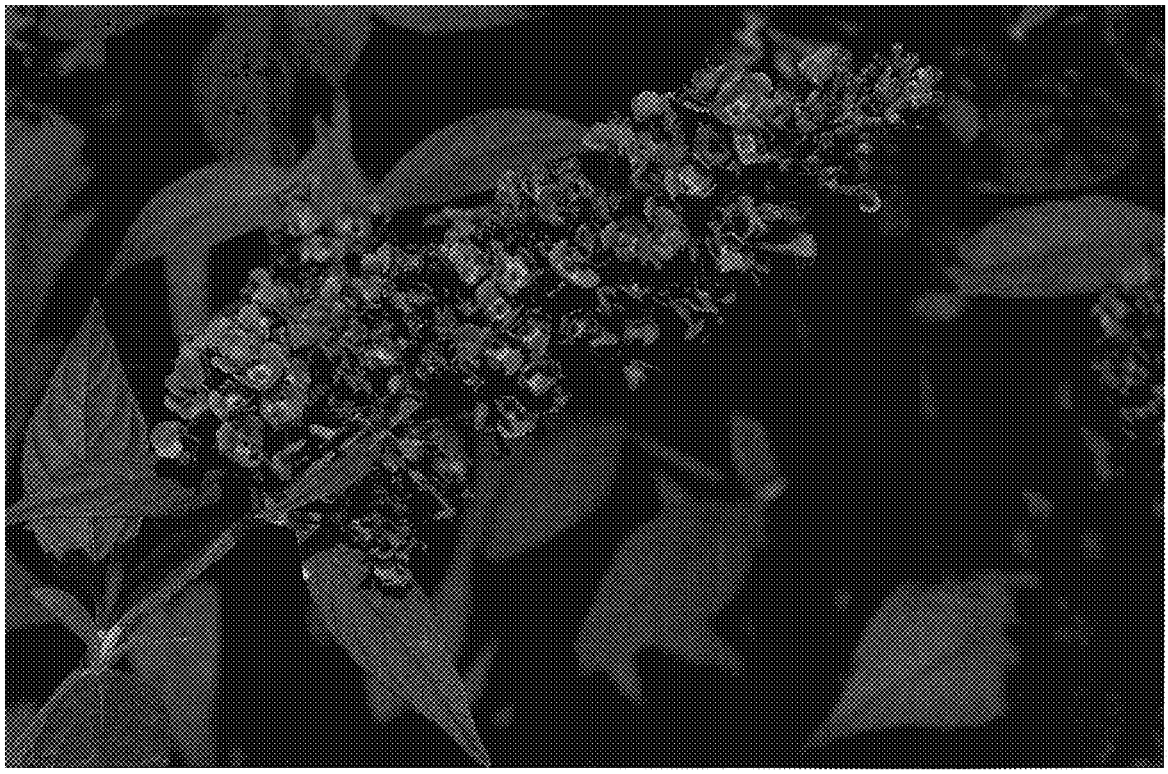
FIG. 2 shows a close-up view of the inflorescence of 'BLUE CHIP', showing the blue color of the individual flowers in the inflorescence.
Figure 3:
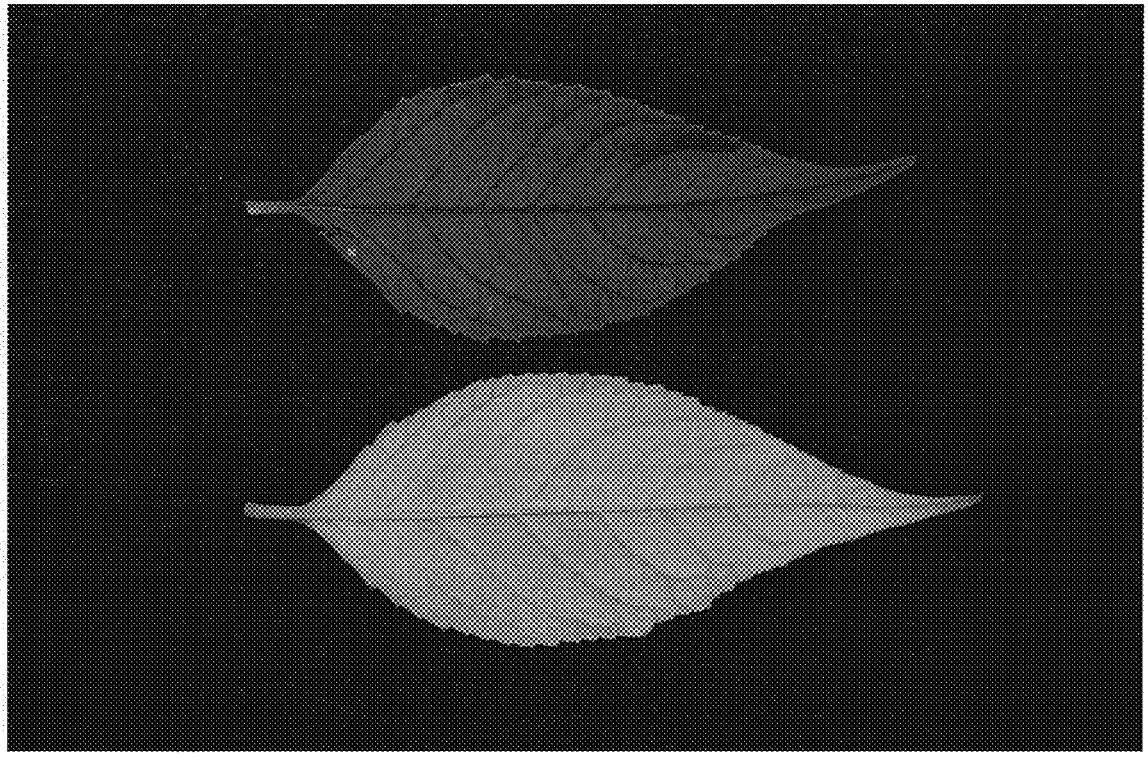
FIG. 3 shows the typical coloration and form of leaves of 'BLUE CHIP'.

This figure shows the lower and upper leaf surface.

DETAILED BOTANICAL DESCRIPTION OF THE VARIETY

The following is a detailed description of the botanical and ornamental characteristics of the subject butterfly bush 'BLUE CHIP'. Color data are based on The Royal Horticultural Society Colour Chart, The Royal Horticultural Society, London, 2001 edition. Where dimensions, sizes, colors and other characteristics are given, it is to be understood that such characteristics are approximations of averages set forth as accurately as practicable.

The descriptions reported herein are from two-year-old specimens grown out-of-doors in Raleigh, N.C.

Genus: *Buddleja.*

Species: Complex hybrid, including *davidii, globosa,* and *lindleyana.*

Denomination: 'BLUE CHIP'.

Commercial Classification: Shrub, deciduous.

Common name: Butterfly bush.

Type: Ornamental.

Uses: Patio container plant, herbaceous perennial border, or shrub border for residential and commercial landscapes.

Cultural requirements: Full sun exposure, well-drained soil, and moderate moisture.

Parentage: 'BLUE CHIP' is a third-generation hybrid that resulted from the original cross pollination of the following *Buddleja* parents: Seed parent='Honeycomb' Pollen parent=hybrid of 'Nanho Purple'×*Buddleja lindleyana*.

Plant description:

*Blooming period.*—Spring, summer, and early fall until frost.

*Blooming habit.*—Spreading to semi-upright with narrow flowers.

*Vigor.*—Low vigor.

*Plant habit.*—Compact, spreading habit.

*Height and spread.*—0.46 meters (height) and 1.4 meters (width).

*Hardiness.*—To date, hardy to minus 8 degrees Centigrade. Not tested below this temperature. Anticipated adapted from USDA hardiness zones 5–9.

*Propagation.*—Softwood to semi-hardwood cuttings under intermittent mist. Roots typically form in 2–3 weeks.

*Root system.*—Fibrous.

*Seasonal interest.*—Blue flowers in spring, summer, and fall on a compact shrub.

*Disease and pest susceptibility and resistance.*—No particular susceptibility or resistance, except occasionally susceptible to spider mites under very hot and dry conditions.

*Special growing requirements.*—Severe yearly pruning in late winter or early spring prior to bud break is recommended to encourage more profuse flowering.

Stems:

*Shape.*—Stem cross section is quadrangular.

*Length.*—Average 55 cm.

*Color.*—Yellow-green (RHS 144C) on recently formed shoots.

*Diameter.*—2–5 mm. near terminal portion of stem, and 8 mm. near base of stem.

*Stem surface.*—Glaucous with slight pubescence.

*Pubescence.*—Sparse.

*Internode length.*—3.6 cm. between nodes

Foliage:

*Type.*—Deciduous.

*Leaf arrangement.*—Opposite, decussate.

*Leaf division.*—Simple.

*Leaf shape.*—Elliptic.

*Leaf base.*—Attenuate.

*Leaf apex.*—Acuminate.

*Leaf venation.*—Pinnate.

*Leaf surface* (*abaxial*).—Glaucous.

*Leaf margin.*—Serrulate.

*Leaf attachment.*—Petiolate.

*Petiole dimensions.*—6.0 mm length. 1.0 mm. width.

*Petiole shape.*—Sulcate.

*Petiole color.*—Grayed-green (RHS 195A).

*Leaf color.*—Adaxial side=green (RHS 137A). Abaxial side=grayed-green (RHS 191B).

*Leaf length.*—Average length (10 leaves)=9.5 cm.

*Leaf width.*—Average width (10 leaves)=3.6 cm.

*Foliar fragrance.*—None detectable.

Flowers:

*Inflorescence.*—Terminal panicle.

*Petals.*—4 (occasionally 5) in number.

*Fused or unfused.*—Fused at base.

*Petal margin.*—Entire.

*Petal apex.*—Rounded lobes, serrulate.

*Petal base.*—Truncate.

*Petal surfaces.*—Glaucous.

*Petal shape.*—Rotund.

*Petal dimensions.*—11 mm. length. 4.0 mm. width.

*Petal color.*—Adaxial and abaxial surface=violet-blue (RHS 90C). Flower shape: Salverform.

*Corolla tube color.*—Inside surface=orange (RHS 25B).

*Corolla tube surfaces* (*inner and outer surfaces*).—Pubescent.

*Corolla tube shape.*—Tubular.

*Color of peduncle.*—Grayed-green (RHS 194A).

*Peduncle surface.*—Glaucous.

*Peduncle length.*—2.4 cm.

*Peduncle shape.*—Flattened oval in cross section.

*Pedicel dimensions.*—1.0 mm. in length and less than 1 mm. in diameter.

*Pedicel color.*—Grayed-green (RHS 194A).

*Pedicel shape.*—Flattened oval in cross section.

*Pedicel surface.*—Glaucous.

*Flowers persistent or self-cleaning.*—Flowers are persistent.

*Lastingness of the overall inflorescence.*—3–4 weeks.

*Lastingness of an individual flower.*—3–5 days.

*Dimensions of inflorescence.*—7.8 cm. in length. 3.2 cm. in diameter.

*Dimensions of entire individual flower.*—12 mm. length. Diameter 6.0 mm. at apex tapering to 1 mm. at base.

*Quantity of flowers.*—198 flowers per individual inflorescence (average of 5 panicles).

*Bud color.*—Violet-blue (RHS 90B to 90C).

*Bud apex.*—Rounded.

*Bud surface.*—Glabrous.

*Bud shape.*—Elongated, linear balloon.

*Calyx shape.*—Tubular.

*Calyx dimensions.*—2.0 mm. in width and 4.0 mm. in length.

*Sepals.*—Four in number.

*Sepal shape.*—Lanceolate.

*Sepal apex.*—Acute.

*Sepal margin.*—Entire.

*Sepal surface.*—Glabrous.

*Sepal color.*—Grayed-green (RHS 194B).

*Flower fragrance.*—Distinct sweet fragrance.

Reproductive organs:

*Stamens.*—Four, fused to inside of petals.

*Anther shape.*—Oblong.

*Anther dimensions.*—1 mm. in length and 0.2 mm. wide.

*Filament size.*—3 mm. in length and less than 0.5 mm. in width.

*Filament color.*—Yellow-white (RHS 158B).

*Pollen amount.*—None produced.

*Pollen color.*—Not applicable. None produced.

*Pistil.*—One in number.

*Pistil dimensions.*—3 mm. in length, and less than 1 mm. in diameter.

*Stigma color.*—Yellow-green (RHS 144A).

*Ovary.*—Present, but often malformed.

*Ovary position.*—Superior.

*Ovary shape.*—Oval.

*Fertility.*—Self-unfruitful. Requires cross pollination. Male sterile, and low female fertility.

Fruit:

*Type.*—Swelled capsule.

*Dimensions.*—3.0 mm. in length (variable) and 1.6 mm. in diameter (variable).

*Color.*—Yellow-green (RHS 144C) when immature.

That which is claimed is:

1. A new and distinct variety of butterfly bush tree (*Buddleja*) substantially as illustrated and described, characterized by its compact growth habit, multi-branched stems, grayed-green leaf color, and blue flower color.

* * * * *